(12) United States Patent
Sciacchitano et al.

(10) Patent No.: US 10,045,899 B2
(45) Date of Patent: Aug. 14, 2018

(54) MODULAR AND FULLY TRACEABLE DELIVERY SYSTEM

(71) Applicant: Capsa Solutions LLC, Portland, OR (US)

(72) Inventors: Maro Sciacchitano, Portland, OR (US); Aubrey Jones, Estacada, OR (US); Chris Miller, Denver, NC (US); Rody Hardy, Portland, OR (US)

( * ) Notice: Subject to any disclaimer, the term of this patent is extended or adjusted under 35 U.S.C. 154(b) by 116 days.

(21) Appl. No.: 15/374,436

(22) Filed: Dec. 9, 2016

(65) Prior Publication Data

US 2018/0008497 A1    Jan. 11, 2018

Related U.S. Application Data

(60) Provisional application No. 62/358,957, filed on Jul. 6, 2016.

(51) Int. Cl.

| | | |
|---|---|---|
| *A61G 12/00* | (2006.01) | |
| *E05B 47/00* | (2006.01) | |
| *A47B 31/00* | (2006.01) | |
| *B62B 3/00* | (2006.01) | |
| *A47B 88/969* | (2017.01) | |
| *A61B 50/13* | (2016.01) | |
| *A61B 50/18* | (2016.01) | |
| *B62B 5/00* | (2006.01) | |
| *G06F 19/00* | (2018.01) | |
| *E05B 65/44* | (2006.01) | |

(52) U.S. Cl.
CPC ............ *A61G 12/001* (2013.01); *A47B 31/00* (2013.01); *A47B 88/969* (2017.01); *A61B 50/13* (2016.02); *A61B 50/18* (2016.02); *B62B 3/005* (2013.01); *B62B 5/0096* (2013.01); *E05B 47/0001* (2013.01); *E05B 65/44* (2013.01); *G06F 19/3456* (2013.01); *A47B 2031/003* (2013.01); *A47B 2031/006* (2013.01); *A47B 2210/08* (2013.01); *A47B 2220/0077* (2013.01); *A61B 2050/185* (2016.02); *A61G 2203/20* (2013.01); *A61G 2205/60* (2013.01)

(58) Field of Classification Search
CPC ...... A61G 12/001; A61B 50/13; A61B 50/18; E05B 47/0001; E05B 65/44; B62B 5/0096; B62B 3/005; A47B 88/969; A47B 31/00; G06F 19/3456
USPC .................................................. 700/231–244
See application file for complete search history.

(56) References Cited

U.S. PATENT DOCUMENTS

| | | |
|---|---|---|
| 5,069,511 A | 12/1991 | Swets et al. |
| 5,205,628 A | 4/1993 | Swets et al. |

(Continued)

FOREIGN PATENT DOCUMENTS

EP       0455862 A2    11/1991

*Primary Examiner* — Michael Collins
(74) *Attorney, Agent, or Firm* — Standley Law Group LLP

(57) ABSTRACT

The exemplary embodiments herein provide a medical cart having a drawer with a post which extends upwardly from a bottom surface of the drawer. The cart further includes a removable medication delivery module having four sidewalls and a bottom wall as well as a plurality of individually-lockable bins placed above the bottom wall and within the four sidewalls. A lock may be positioned above the bottom wall and below the plurality of individually-lockable bins with an aperture on the lock which engages with the post and a hole in the bottom wall sized to accept the post.

19 Claims, 17 Drawing Sheets

(56) References Cited

U.S. PATENT DOCUMENTS

| | | | |
|---|---|---|---|
| 5,314,244 A | 5/1994 | Swets et al. | |
| 5,745,366 A | 4/1998 | Highman et al. | |
| 5,805,456 A | 9/1998 | Highman et al. | |
| 5,883,806 A | 3/1999 | Meador et al. | |
| 5,905,653 A | 5/1999 | Highman et al. | |
| 7,630,791 B2* | 12/2009 | Nguyen | A61G 12/001 700/236 |
| 7,909,418 B2* | 3/2011 | McFarland | G07F 17/0092 312/215 |
| 8,061,790 B2* | 11/2011 | Anikhindi | F25D 25/025 312/319.5 |
| 8,332,066 B2* | 12/2012 | Weber | G07F 11/62 221/5 |
| 8,335,588 B2* | 12/2012 | Rahilly | E05B 65/46 221/156 |
| 8,662,606 B2* | 3/2014 | Santmyer | G07F 11/62 312/319.7 |
| 8,700,211 B2* | 4/2014 | Shoenfeld | A47B 88/90 221/151 |
| 8,701,931 B2* | 4/2014 | Santmyer | G07F 17/14 221/1 |
| 8,983,664 B2* | 3/2015 | Rahilly | E05B 65/46 700/231 |
| 9,078,520 B2* | 7/2015 | Shoenfeld | A47B 81/00 |
| 2003/0201697 A1 | 10/2003 | Richardson | |
| 2003/0222548 A1 | 12/2003 | Richardson et al. | |
| 2011/0101018 A1* | 5/2011 | Shafir | A47F 1/00 221/1 |
| 2012/0191241 A1* | 7/2012 | Rahilly | G07G 1/0027 700/231 |
| 2012/0203377 A1 | 8/2012 | Paydar et al. | |
| 2014/0300116 A1* | 10/2014 | Hellwig | E05B 47/0001 292/336.3 |

\* cited by examiner

US 10,045,899 B2

MODULAR AND FULLY TRACEABLE DELIVERY SYSTEM

CROSS-REFERENCE TO RELATED APPLICATIONS

This application claims priority to U.S. Provisional Application No. 62/358,957 filed on Jul. 6, 2016 which is herein incorporated by reference in its entirety.

TECHNICAL FIELD

Embodiments generally relate to modular and fully traceable systems for delivering healthcare supplies, including but not limited to medications and instruments.

BACKGROUND OF THE ART

The transporting, storing, dispensing, and returning/disposal of medical supplies and medications is a daunting task in view of the complexity of modern healthcare systems. Any system or method for serving this industry must provide security and traceability, as well as provide an easy platform for incorporating the system into the daily routine for healthcare professionals.

SUMMARY OF THE EXEMPLARY EMBODIMENTS

The exemplary embodiments herein provide a medical cart having a drawer with a post which extends upwardly from a bottom surface of the drawer. The cart further includes a removable medication delivery module having four sidewalls and a bottom wall as well as a plurality of individually-lockable bins placed above the bottom wall and within the four sidewalls. A lock may be positioned above the bottom wall and below the plurality of individually-lockable bins with an aperture on the lock which engages with the post and a hole in the bottom wall sized to accept the post.

The foregoing and other features and advantages of the present invention will be apparent from the following more detailed description of the particular embodiments, as illustrated in the accompanying drawings.

BRIEF DESCRIPTION OF THE DRAWINGS

A better understanding of an exemplary embodiment will be obtained from a reading of the following detailed description and the accompanying drawings wherein identical reference characters refer to identical parts and in which.

DETAILED DESCRIPTION

Figure 1A:
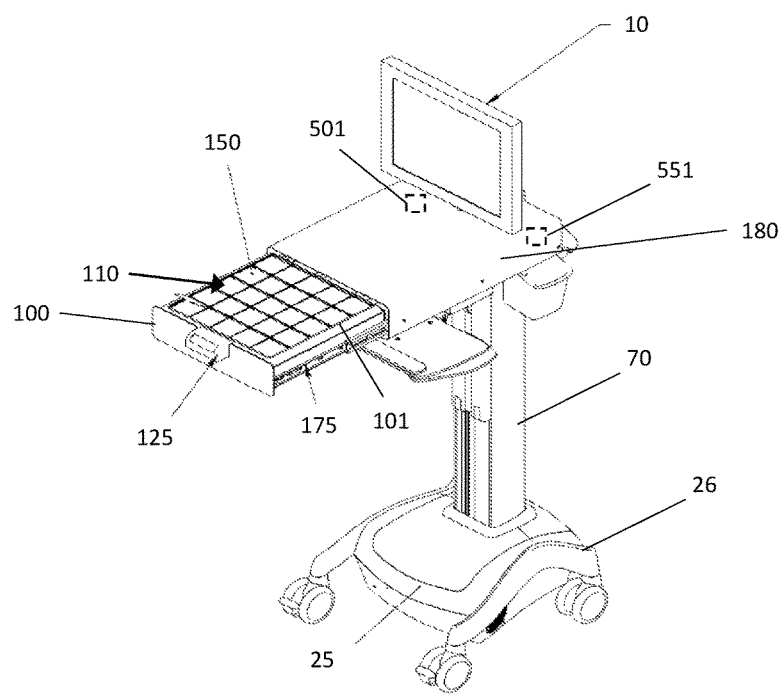
FIG. 1A is a perspective illustration of an exemplary embodiment of a medical cart, having an exposed central column.

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1A is a perspective illustration of an exemplary embodiment of a medical cart, having an exposed central column 70. The cart is supported by a base 26 which preferably contains a set of wheels or casters for moving the cart. A battery 25 and associated electronics may be placed within the base 26 and is electrically connected through the central column 70 to a computer 10, which includes a display, processor, and memory. In some embodiments, the computer 10 may be a touch screen and will contain the processor and memory within the housing for the display touch screen. In other embodiments, the computer 10 may have a display positioned as shown in the figure, with a processor and memory being placed somewhere else on the cart.

A sleeve 180 extends from the cart and away from the column 70, to provide an envelope for accepting a drawer 101. Preferably, a pair of drawer slides 175 are used to allow the drawer 101 to be translated in/out of the sleeve 180. A delivery module 110 can be inserted/removed from the drawer 101, and preferably contains a plurality of bins 150 which are preferably individually-lockable and trackable. A protrusion 125 preferably extends from the delivery module 110 and out of the drawer 101. The protrusion 125 preferably extends away from the front facia 100 of the drawer 101.

A wireless power transmitter 501 is placed on the cart to communicate with a wireless power receiver 500 as described below. The wireless power transmitter 501 is preferably in electrical connection with the battery 25 and associated electronics found within the base 26. A wireless data transmitter/receiver 551 is also placed on the cart to communicate with a wireless data transmitter/receiver 550 as described below. The wireless data transmitter/receiver 551 is preferably in electrical connection with the computer 10 and its associated processor.

Figure 1B:
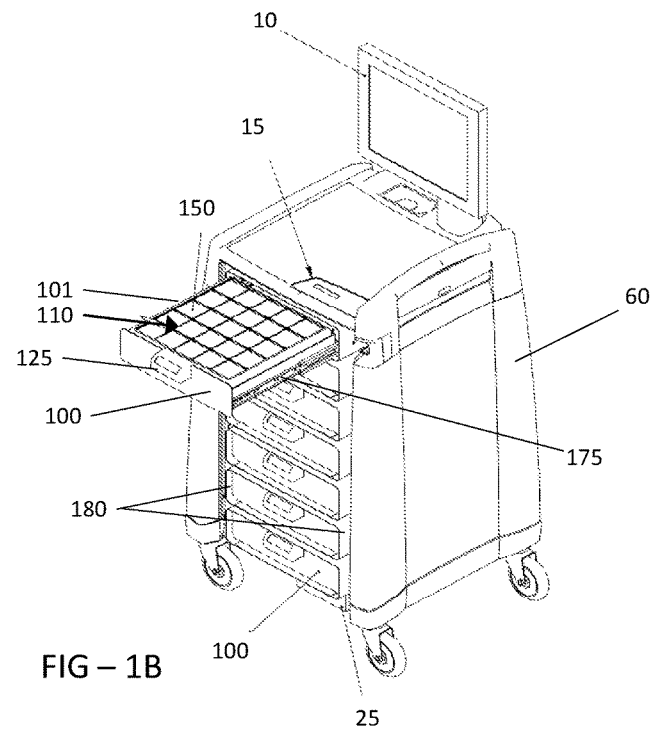
FIG. 1B is a perspective illustration of another exemplary embodiment of a medical cart, having a housing which contains a plurality of sleeves.

FIG. 1B is a perspective illustration of another exemplary embodiment of a medical cart, having a housing 60 which contains a plurality of sleeves 180. In this embodiment, the column 70 may be placed inside the housing 60 or may not be used at all. A battery 25 and associated electronics may be placed below the housing 60 or within a bottom portion of the housing 60 and would again be in electrical connection with the computer 10. In this embodiment, a user interface 15 may be placed on or near the top surface of the housing 60, and allows the user to input various types of identifying information, such as biometrics (finger print, retina scan, hand print, etc.) or a key card (magnetic strip, RFID, etc.) for gaining access to the cart generally. As will be described below, access to particular drawers 101 or even specific bins 150 within a drawer may still be restricted, even after general access to the cart has been given. The sleeves 180 preferably have a rectangular cross-section and may completely cover the top, sides, and bottom of the delivery module 110.

Figure 2:
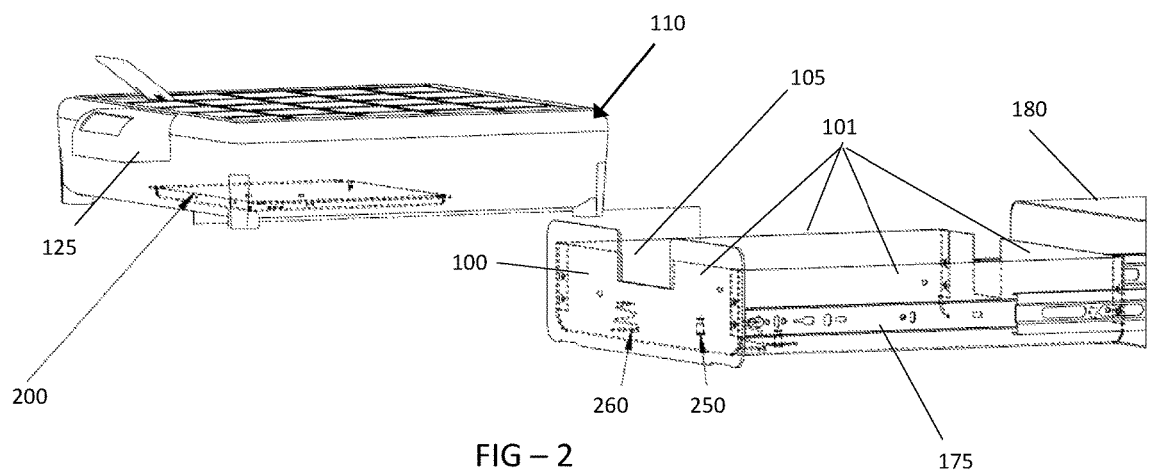
FIG. 2 is a perspective view of an exemplary embodiment for inserting and removing the delivery module from the sleeves.

FIG. 2 is a perspective view of an exemplary embodiment for inserting and removing the delivery module 110 from the drawers 101 within the sleeves 180. As shown, the drawer 101 may be translated out of the sleeve 180 until the rear wall of the drawer 101 is nearly outside of the sleeve 180. The delivery module 110 can then be lowered vertically into the drawer 101, until the locking mechanism 200 is engaged to lock the delivery module 110 within the drawer 101. One or more springs 260 may be placed on the bottom surface of the drawer 101, where the spring 260 could be any type of compression spring, leaf spring, or other type of spring that would simply bias the delivery module 110 upwardly and away from the bottom of the drawer 101. One or more posts 250 also preferably extend from the bottom surface of the drawer 101.

As described further below, the posts 250 should be sized and positioned to engage with the locking mechanism 200 to secure the delivery module 110 within the drawer 101. In an exemplary embodiment, a front facia 100 may be positioned outside of the drawer 101 and on the front surface of the drawer 101, where the facia 100 has a surface area that is larger than the surface area of the front surface of the drawer 101, and where the facia 100 is sized to fit within the sleeve 180.

Figure 3:
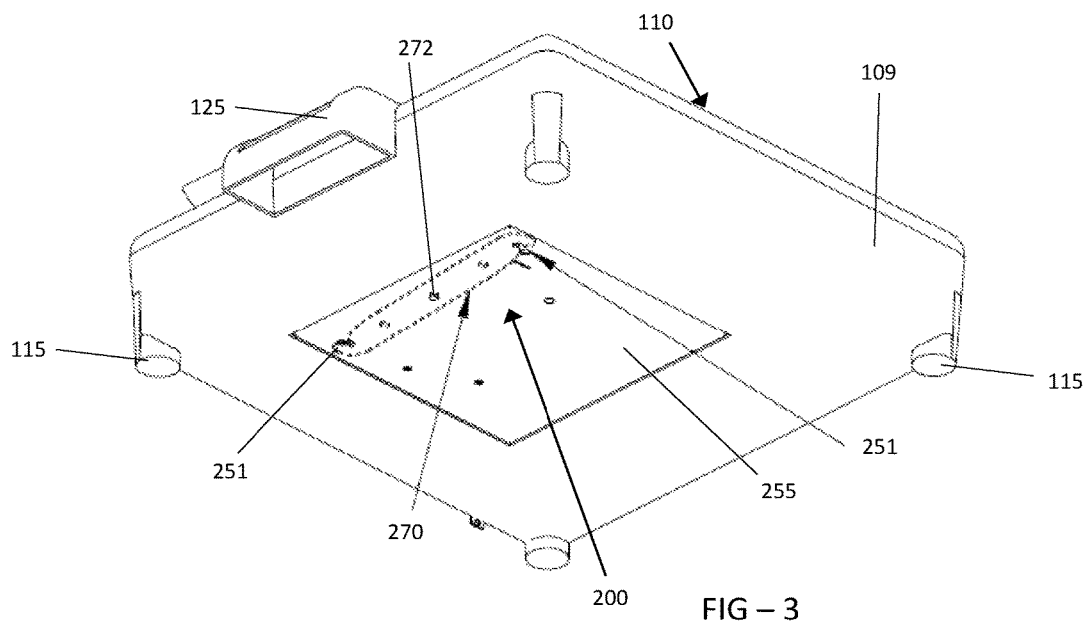
FIG. 3 is a bottom perspective view of the embodiment of the delivery module shown in FIG. 2.

FIG. 3 is a bottom perspective view of the embodiment of the delivery module 110 shown in FIG. 2. A plurality of short pillars 115 may extend from the bottom surface 109 of the delivery module 110. Aligned generally with the bottom surface 109 is an optional bottom plate 255, which covers the locking mechanism 200, which preferably comprises a lock 270 which rotates about a pivot point 272, which is preferably near the center of the lock 270. The lock 270 can take on many forms, but is preferably elongate with a pair of apertures on the opposing ends of the lock 270 which engage with the posts 250 in the drawer 101. One or more holes 251 may be positioned to align with each post 250 and accept the post 250 into the delivery module 110, or if the bottom plate 255 is used the holes 251 would be placed within the plate 255 to allow each post 250 to pass through the plate 255.

Figure 4:
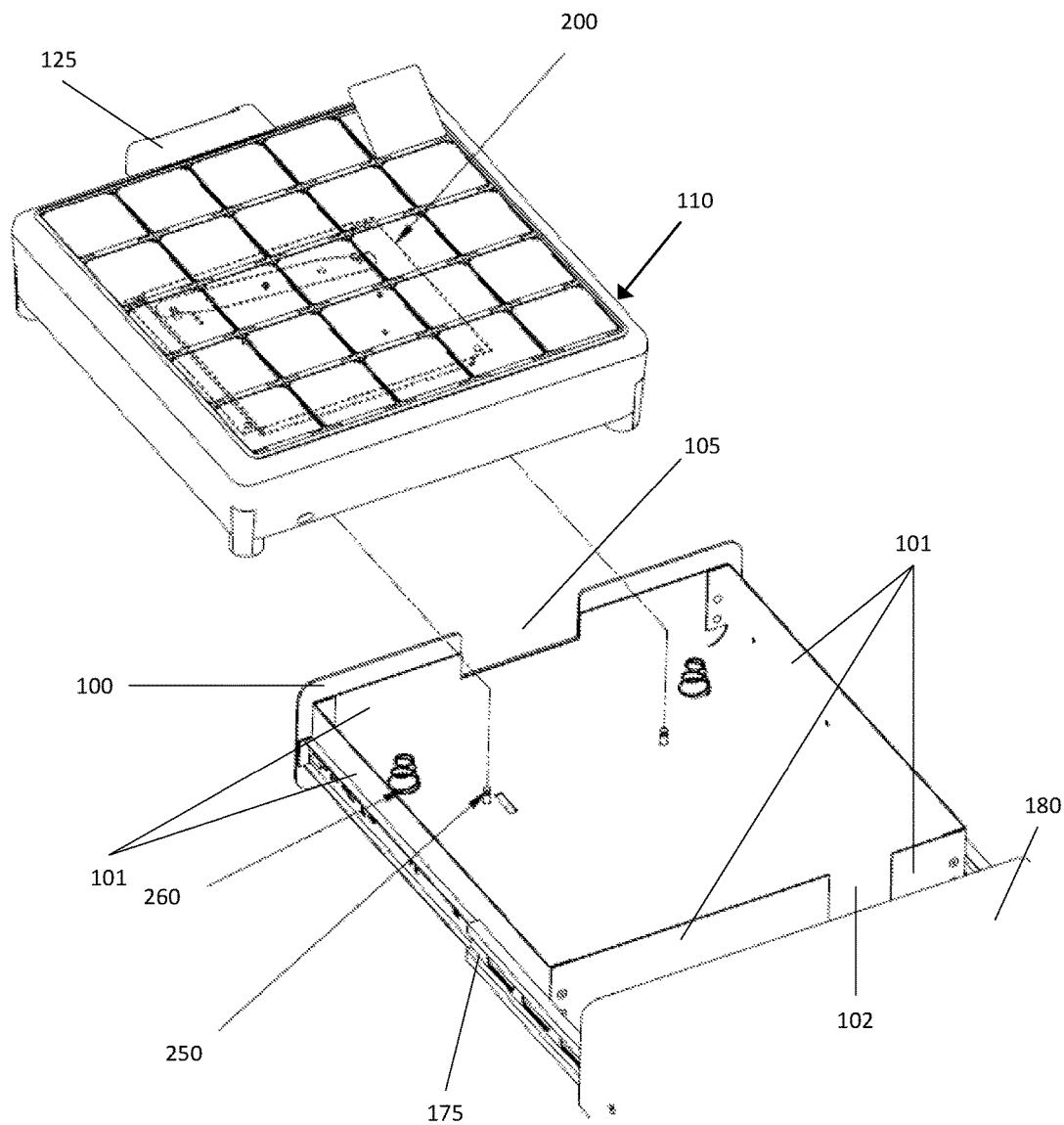
FIG. 4 is a top perspective view of the embodiment shown in FIG. 2.

FIG. 4 is a top perspective view of the embodiment shown in FIG. 2. To install the delivery module 110 within the drawer 101, the posts 250 are aligned with the holes 251 on the bottom of the delivery module 110 as it is lowered into the drawer 101. A notch 105 is preferably located at the front of the drawer 101, and generally comprises a rectangular section of material that is removed from the front wall of the drawer 101. When using the front facia 100, a corresponding rectangular section of material is also preferably removed from the facia 100. In this way, the protrusion 125 is permitted to extend out of the front wall of the drawer 101 and the facia 100 (if used). Another piece of material is preferably removed from the rear wall of the drawer 101 to create the rear wall aperture 102, which is preferably aligned with the wireless power receiver 500.

Figure 5:
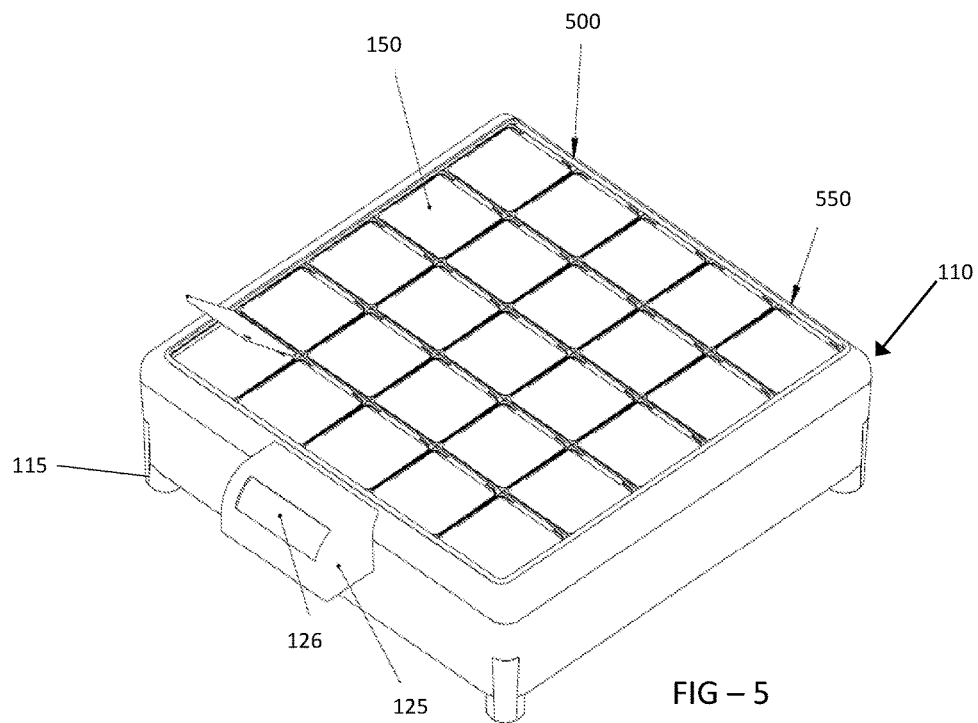
FIG. 5 is a top perspective view of an exemplary embodiment of the delivery module.

FIG. 5 is a top perspective view of an exemplary embodiment of the delivery module 110. On the rear portion of the delivery module 110 may be a wireless power receiver 500 along with a wireless data transmitter/receiver 550. Both the wireless power receiver 500 and the wireless data transmitter/receiver 550 are preferably in electrical connection with the PCB 300. The protrusion 125 preferably contains an electronic display 126 which could be any flat panel display including but not limited to: LCD, OLED, or any form of luminescent polymers. The protrusion 125 preferably begins near the top of the delivery module 110 and extends downwardly until near the midpoint of the vertical height of the delivery module 110. The protrusion 125 is preferably placed near the horizontal midpoint of the delivery module 110.

Figure 6:
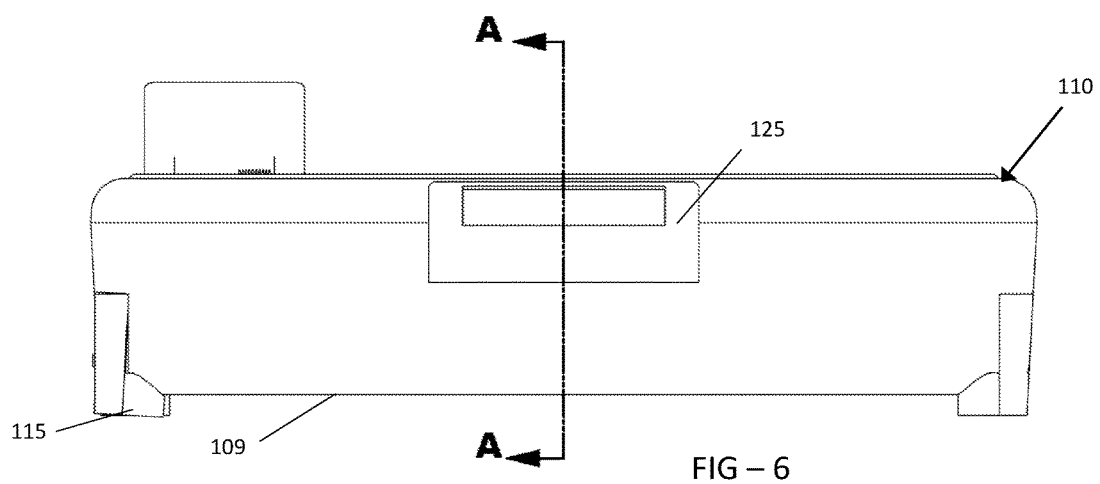
FIG. 6 is a front elevation view of the embodiment of the delivery module shown in FIG. 5 where the section line A-A has been indicated.

FIG. 6 is a front elevation view of the embodiment of the delivery module 110 shown in FIG. 5 where the section line A-A has been indicated. Again it is noted that an exemplary embodiment includes a plurality of short pillars 115 which raise the bottom surface 109 of the delivery module 110 off the bottom surface of the drawer 101. The bottom plate 255 is preferably aligned horizontally with the bottom surface 109. It should be noted that in some embodiments, the bottom plate 255 may not be used, and instead the bottom surface 109 would simply be extended and would provide the structure in this area, such that the lock 272 and spring 295 would simply be attached to the bottom of the delivery module 110. In this type of embodiment, rather than referring to the plate 255 it would be more appropriate to refer to the bottom wall instead, which could reference both use of a plate as well as simply extending the bottom surface 109 of the delivery module 110.

Figure 7:
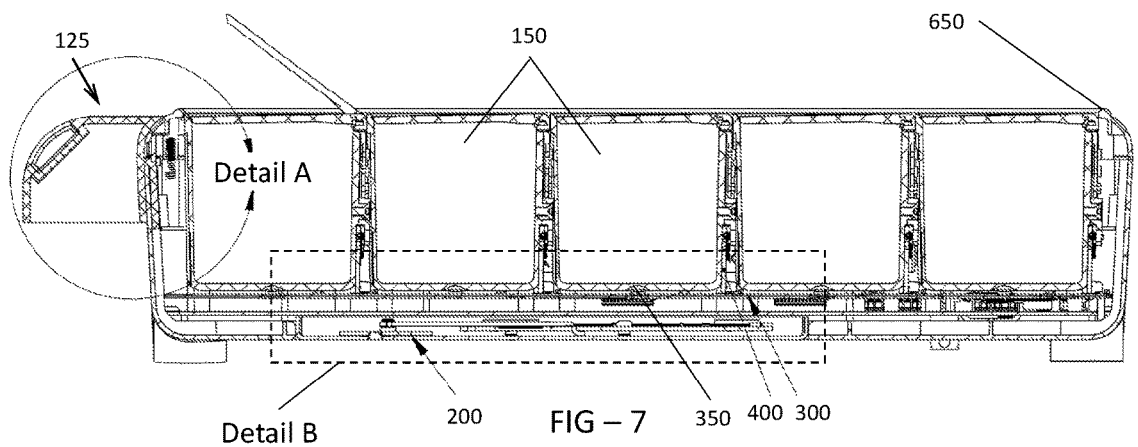
FIG. 7 is a side section view, taken along section line A-A and indicating the location of Detail A and Detail B.

FIG. 7 is a side section view, taken along section line A-A and indicating the location of Detail A. A printed circuit board 300 (PCB) is preferably positioned under the bins 150 and generally has at least a portion of the PCB 300 underneath each bin 150. The PCB 300 includes a number of different components and circuits, which can vary depending on the particular embodiment. Generally speaking, the PCB 300 would at least include a processor and electronic data storage. Each bin 150 should contain its own electromechanical actuator 400, which is used to lock each bin 150 individually. The actuator 400 may be an SMA wire actuator or motor and is preferably placed in between adjacent bins 150 and is not underneath the bin 150, but this is not required. An illuminating device 350 may be placed underneath each bin 150 or incorporated into the bottom of each bin 150. The illuminating device 350 is preferably one or more light emitting diodes (LEDs), ideally a grouping that includes a red, a green, and a blue LED, but can also be an electroluminescent polymer. The actuator 400 and illuminating device 350 of each bin 150 is preferably in electrical connection with the PCB 300, which is in turn in electrical connection with the wireless data transmitter/receiver 550.

Figure 8:
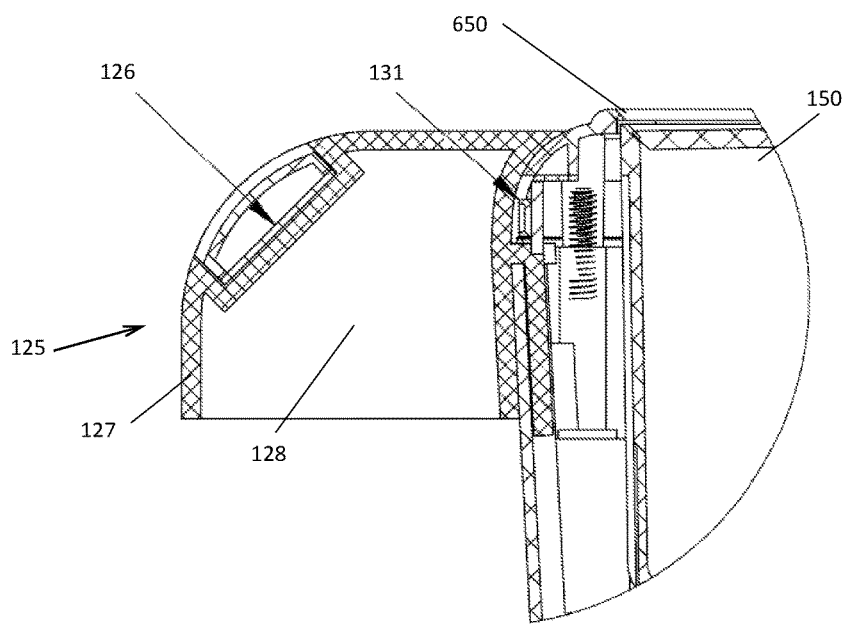
FIG. 8 is a detailed section view of Detail A.

FIG. 8 is a detailed section view of Detail A. An exemplary protrusion 125 may contain a sidewall portion 127 which begins at the top of the front face of the delivery module 110 and then extends horizontally and away from the delivery module 110. The sidewall portion 127 then contains an arc or radius such that the sidewall portion 127 turns downwardly until travelling substantially vertically until reaching the distal end, which is preferably near the midpoint of the vertical height of the delivery module 110. This exemplary protrusion 125 also preferably contains an opening or hollow portion 128 which is defined by the space below the sidewall portion 127 and between the sidewall portion 127 and the front face of the delivery module 110.

Another illuminating device 131 may be placed within the front wall of the delivery module 110, so that it can illuminate the opening 128. In the embodiment shown, the illuminating device 131 is positioned behind a portion of the sidewall 127 which, in this embodiment, also runs parallel to the front wall of the delivery module 110. In this situation, it is preferable that the sidewall 127 either contains a physical opening to allow the light to pass through the sidewall 127. Alternatively, the sidewall 127 can be constructed with a translucent, semi-translucent, or transparent material that would allow the light to pass through the sidewall 127. The illuminating device 131 is preferably one or more light emitting diodes (LEDs), ideally a grouping that includes a red, a green, and a blue LED, but can also be an electroluminescent polymer. The illuminating device 131 and the display 126 are preferably in electrical connection with the PCB 300. In some embodiments, where the sidewall portion 127 has adequate strength, a user can utilize the opening 128 in combination with the sidewall portion 127 as a handle for transporting the delivery module 110. In this way, the opening 128 is sized to accept a portion of several fingers of the user, in order to obtain adequate grip of the sidewall portion 127.

Figure 9:
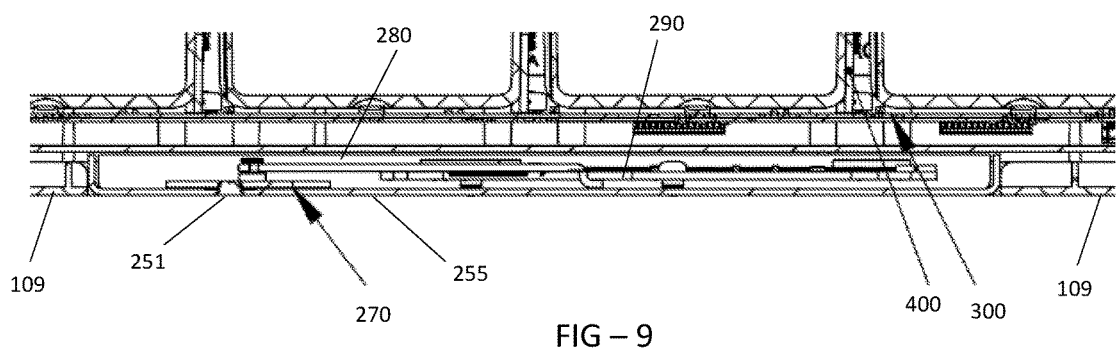
FIG. 9 is a detailed section view of Detail B.

FIG. 9 is a detailed section view of Detail B. The bottom plate 255 is generally co-planar with the bottom surface 109 and in this embodiment the bottom plate 255 has a generally U-shaped cross-section, sized to fit within a rectangular opening in the bottom surface 109. The hole 251 in this embodiment is found within the plate 255, which permits the post 250 to pass through the plate 255 and engage with the lock 270.

Figure 10:
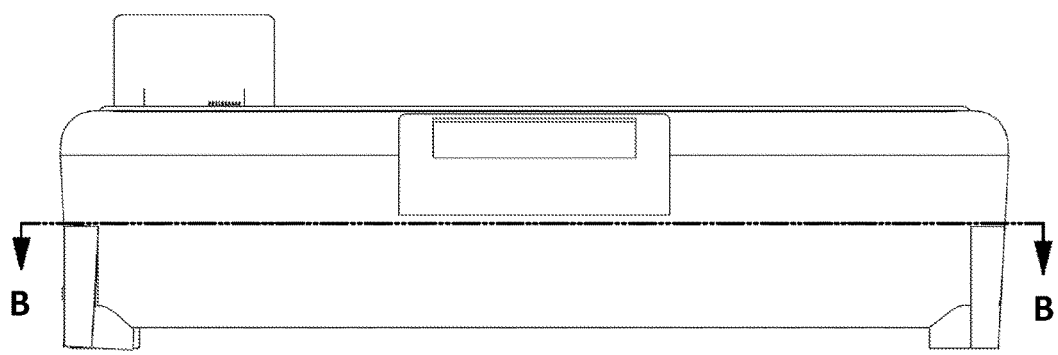
FIG. 10 is a front elevation view of the embodiment of the delivery module shown in FIG. 5 where the section line B-B has been indicated.

FIG. 10 is a front elevation view of the embodiment of the delivery module shown in FIG. 5 where the section line B-B has been indicated.

Figure 11:
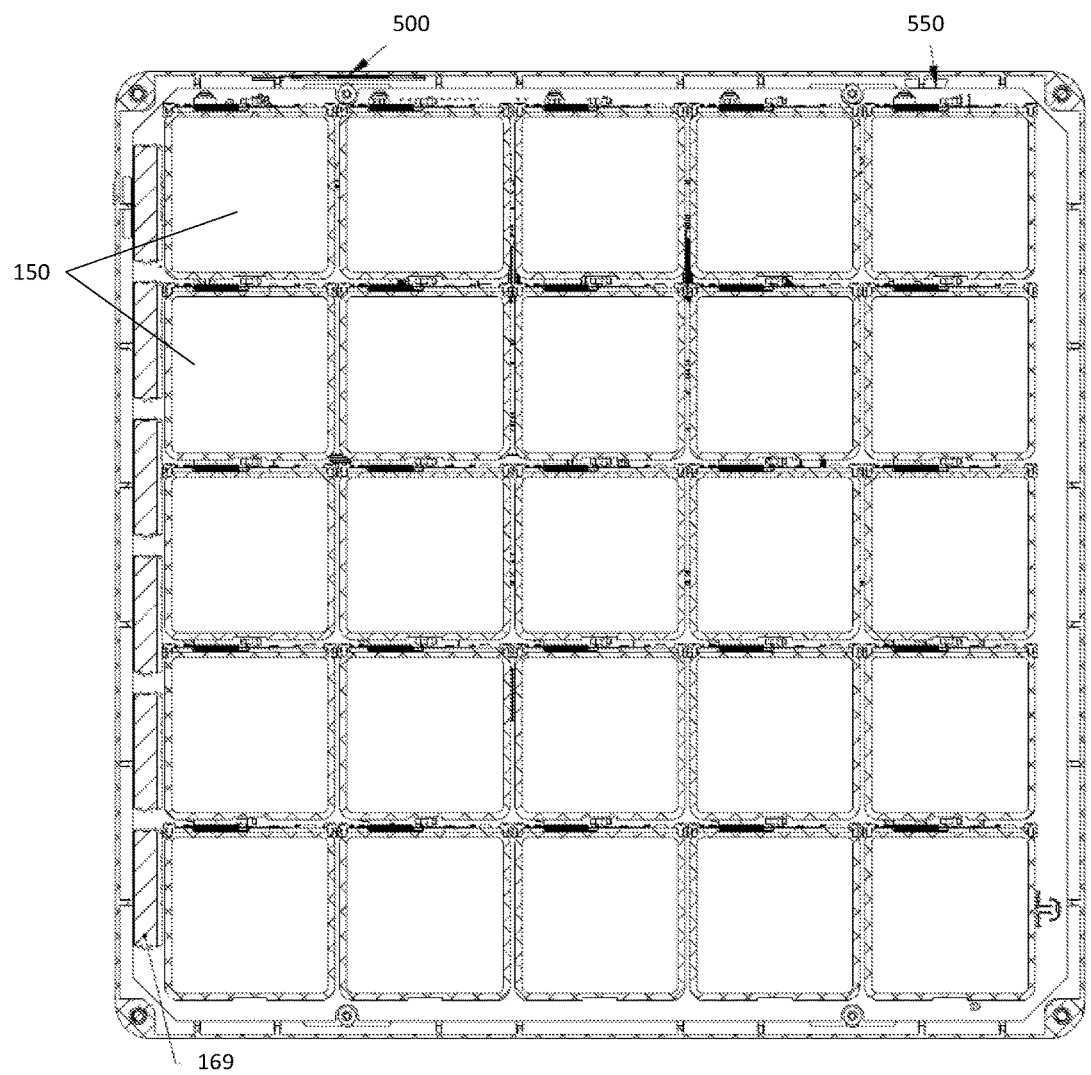
FIG. 11 is a top section view, taken along section line B-B.

FIG. 11 is a top section view, taken along section line B-B. One or more batteries 169 are preferably placed along one or more sides of the delivery module 110. In an exemplary embodiment, the batteries 169 are not placed along the front or rear portions of the delivery module 110. Also in an exemplary embodiment, the battery 169 is positioned between a row of bins 150 and the interior surface of the delivery module 110. The batteries 169 are preferably in electrical connection with the PCB 300, which includes a charging circuit that is in electrical connection with the wireless power receiver 500.

Figure 12:
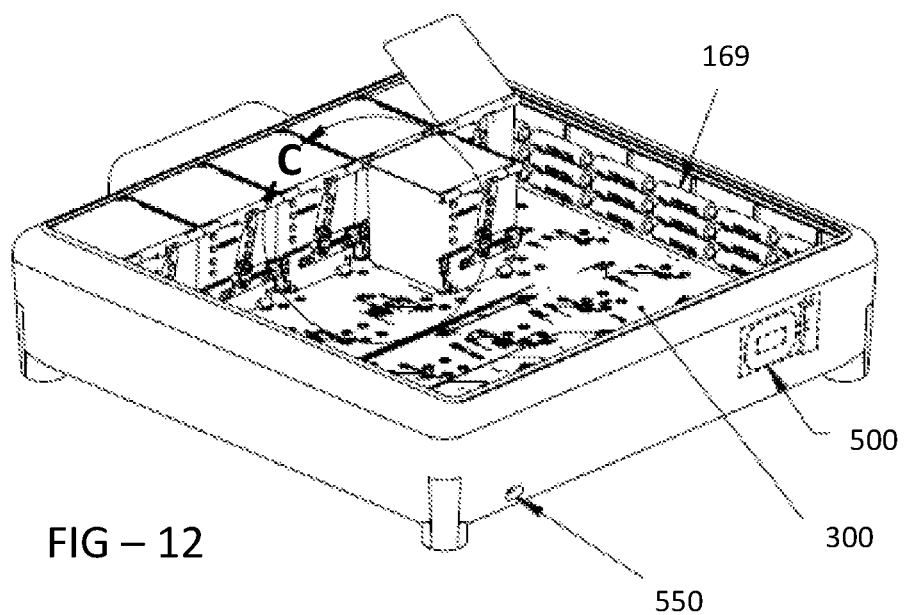
FIG. 12 is a top perspective view of the embodiment of the delivery module shown in FIG. 5 where the delivery module has had several bins removed and where the location for Detail C has been indicated.

FIG. 12 is a top perspective view of the embodiment of the delivery module shown in FIG. 5 where the delivery module has had several bin removed and where the location for Detail C has been indicated. The PCB 300 is preferably underneath each bin 150, and could be a single structure or could be multiple separate PCBs.

Figure 13:
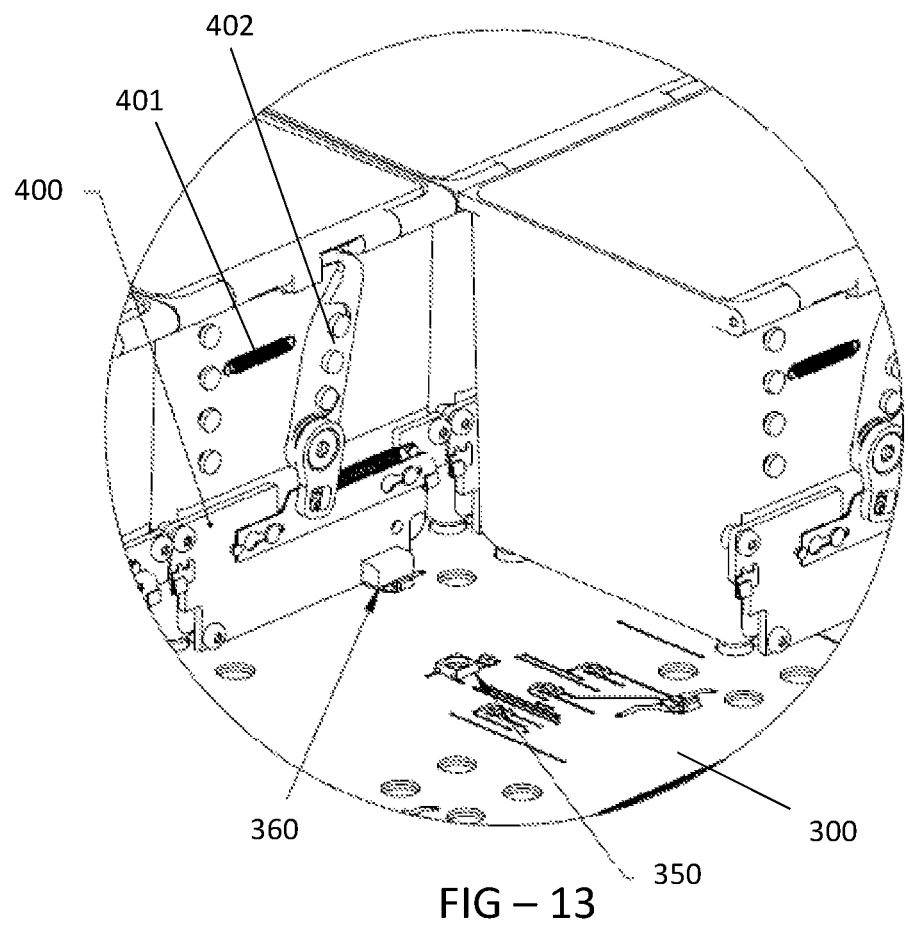
FIG. 13 is a detailed view of Detail C.

FIG. 13 is a detailed view of Detail C. The electromechanical actuator 400 preferably contains a connector 360 which connects with the PCB 300. The illuminating device 350 is preferably mounted atop, and in electrical connection with the PCB 300. Each bin 150 preferably contains a lock 402 which is biased with a spring 401 to be in the locked condition, and requires an electrical actuation in order to be opened. Thus, to lock the bin 150 once it has been opened, the lid 151 is preferably rotated about the hinge 155 until the lock 402 is engaged and the bin 150 is closed and locked, without requiring any electrical actuation. In this way, it can be described as having been mechanically locked, and not electrically locked. Other embodiments may provide for electrically locking the bin 150, but for the exemplary embodiments this would be done mechanically. Further, the locked state can remain, even when power is lost.

Figure 14:
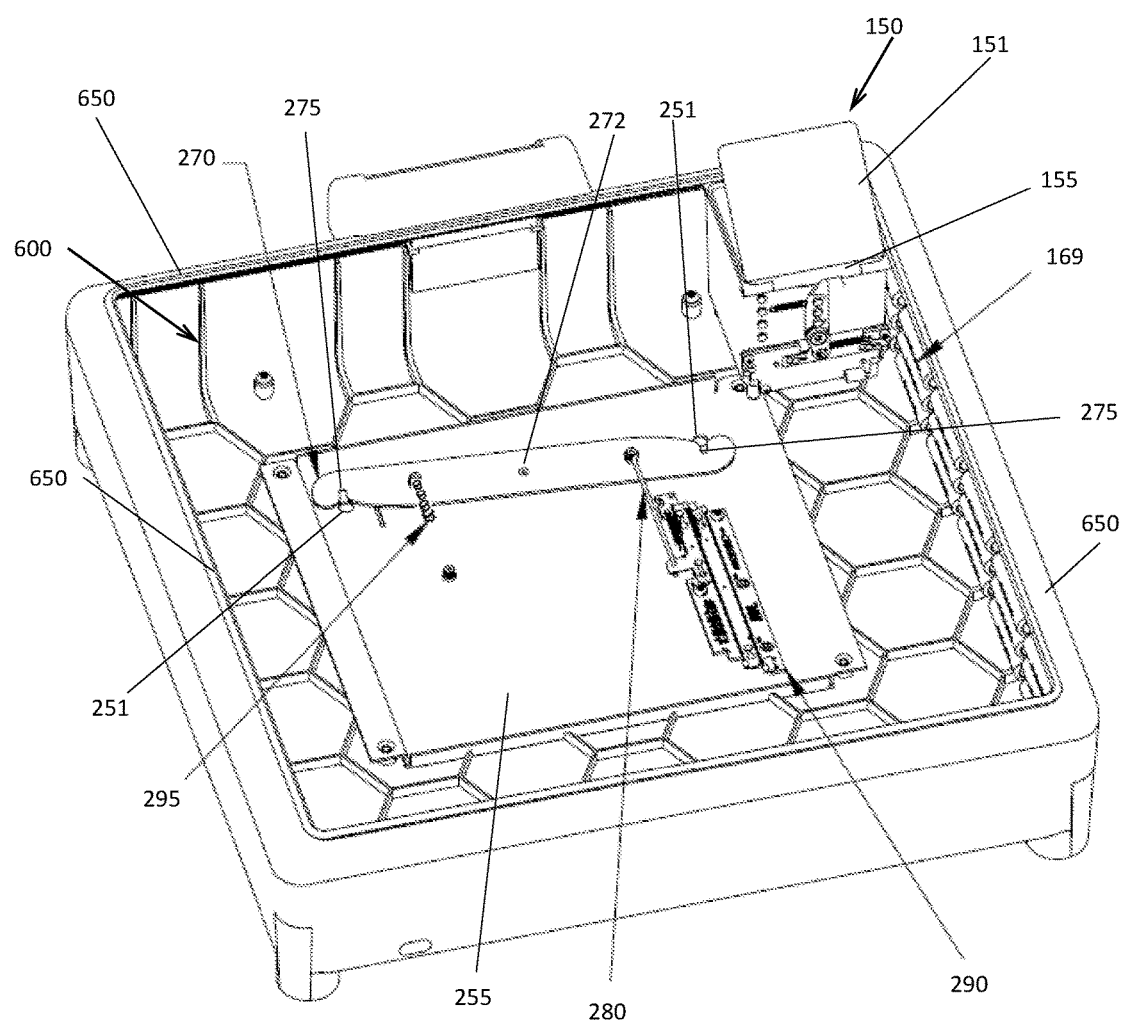
FIG. 14 is a top perspective view of the embodiment of the delivery module shown in FIG. 5 where each bin (except for one) has been removed along with the printed circuit board for the delivery module.

FIG. 14 is a top perspective view of the embodiment of the delivery module shown in FIG. 5 where each bin 150 (except for one) has been removed along with the printed circuit board 300. The lock 270 is preferably pivotally attached to the bottom plate 255 at the pivot point 272. A linkage 280 may be used to connect the lock 270 with an electromechanical actuator 290, which can be an SMA wire actuator or motor. The linkage 280 preferably connects to the lock 270 about halfway in between the pivot point 272 and the aperture 275. A spring 295 may be used to bias the lock 270 in the closed position, so that when the module is pressed downwardly into the drawer, the lock 270 engages mechanically, without requiring any electrical input. In this way, it could be referred to as having been mechanically locked, and not electrically locked. Further, the locked state can remain, even when power is lost.

In this embodiment, a tension spring is attached at one end to the plate 255 and at a second end to the lock 270. It is preferable that the distance from the spring 295 attachment point to the pivot point 272 is substantially the same as the distance from the linkage 280 attachment point to the pivot point 272. In other words, the attachment points for the spring 295 and linkage 280 should be symmetrical about the pivot point 272, although this is not required.

As noted above, the lock 270 preferably contains one or more apertures 275 for accepting a post 250. Here, there are apertures 275 placed on both opposing ends of an elongate lock 270. The apertures 275 are preferably placed above the holes 251 in the plate 255.

From the view of this embodiment, the delivery module 110 could generally be described as having a floor and four sidewalls which define a tray 600, which accepts a plurality of individually lockable bins 150. Preferably, when each bin 150 is closed, it does not extend above the sidewalls 650 of the tray 600. Each bin 150 preferably contains a lid 151 with a hinge 155 that is located on the rear edge of the bin 150 (i.e. opposite the front edge of the delivery module 110 which contains the protrusion 125).

Figure 15:
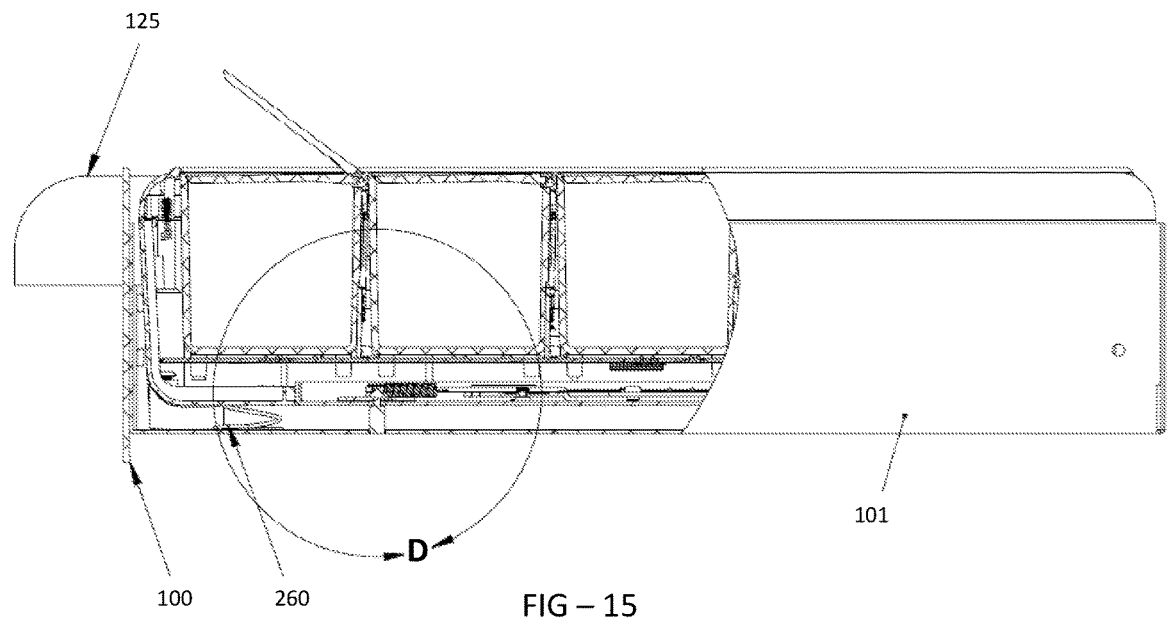
FIG. 15 is a partial section view of an exemplary embodiment of the delivery module when locked within the drawer and where the location for Detail D has been indicated.

FIG. 15 is a partial section view of an exemplary embodiment of the delivery module when locked within the drawer 101 and where the location for Detail D has been indicated.

Figure 16:
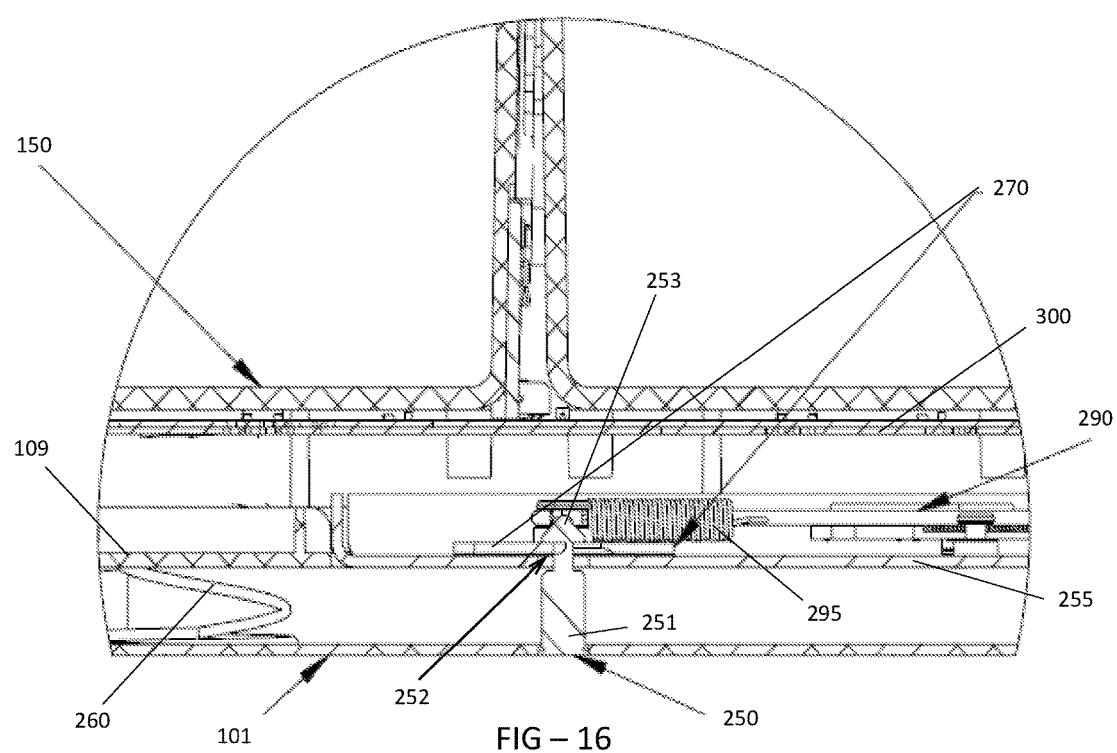
FIG. 16 is a detailed view of Detail D.

FIG. 16 is a detailed view of Detail D. The post 250 extends from the bottom of the drawer 101 with a shaft 251 having a diameter D1. At the top of the shaft 251 there is preferably a shoulder, as shaft 252 extends upwardly from shaft 251 and has a diameter D2, where it is preferred that D2<D1. A tip 253 is preferably attached to the top of shaft 252 and is preferably conical with a base having diameter D3, where it is preferred that D3>D2. In some embodiments, D1 is substantially equal to D3. When the lock 270 is engaged with the post 250, both the lock 270 as well as the bottom plate 255 should preferably surround at least a portion of the shaft 252. In other words, the bottom plate 255 and the lock 270 should be between shaft 251 and the tip 253. A gap is preferably defined between the bottom surface 109 of the delivery module and the bottom of the drawer 101, where the gap is generally defined by the height of the short pillars 115.

Figure 17:
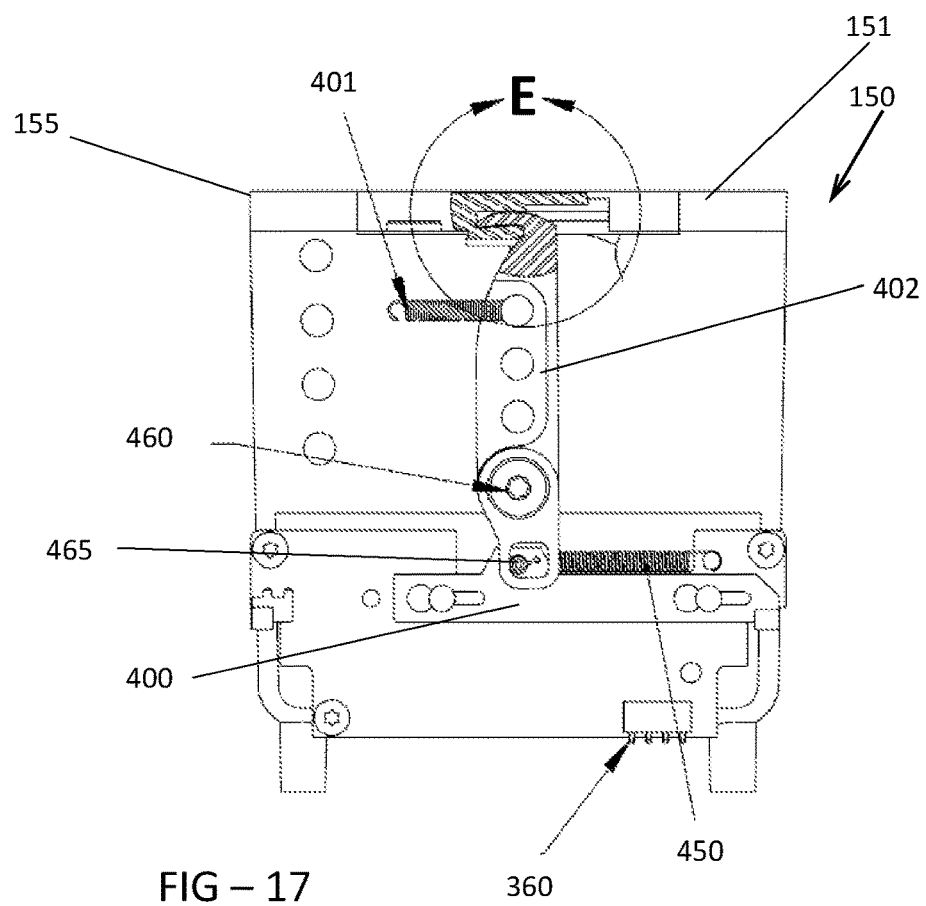
FIG. 17 is a rear partial section view of an exemplary embodiment of a bin where the bin has been locked and where the location for Detail E has been indicated.

FIG. 17 is a rear partial section view of an exemplary embodiment of a bin 150 where the bin has been locked and where the location for Detail E has been indicated. The lock 402 is preferably pivotally attached to the bin 150 at the pivot point 460. The lock 402 is also preferably pivotally attached to the actuator 400 at the pivot point 465. An actuator spring 450 may be attached at a first end to the bin 150 or a piece that is fixed relative to the bin, and attached at a second end to the pivot point 465. In this way, the spring 450 is positioned to bias the lock 402 in a closed position. A lock spring 401 is preferably attached at a first end to the lock 402 and at a second end to the bin 150 or a piece that is fixed relative to the bin 150. In this way, the spring 401 is also preferably positioned to bias the lock 402 in a closed position. Although not required, both springs 450 and 401 are preferably extension springs. Also preferably by not required, springs 450 and 401 are positioned on opposite sides of the lock 402.

Figure 18:
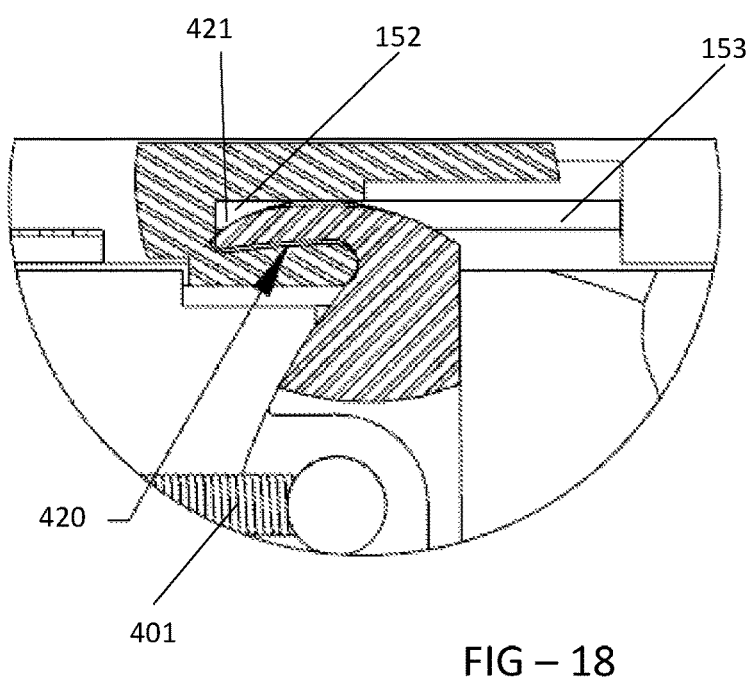
FIG. 18 is detailed view of Detail E.

FIG. 18 is detailed view of Detail E. A hook 420 is preferably located at the top of the lock 402 and preferably contains a rounded tip 421 which is formed at the end of a narrow body. The narrow body preferably fits within a slot 152 in the lid 151. The lid 151 preferably contains an open space 153 which is adjacent to the slot 152 and preferably has a larger cross-sectional area than the slot 152. As shown, when the lock 402 is fully engaged, the narrow body of the hook 420 is inserted into the slot 152 as far as possible, preferably until the rounded tip 421 contacts the deepest point in the slot 152 which may be the same point at which the two opposing rounds of the lid 151 and hook 420 are contacting.

Figure 19:
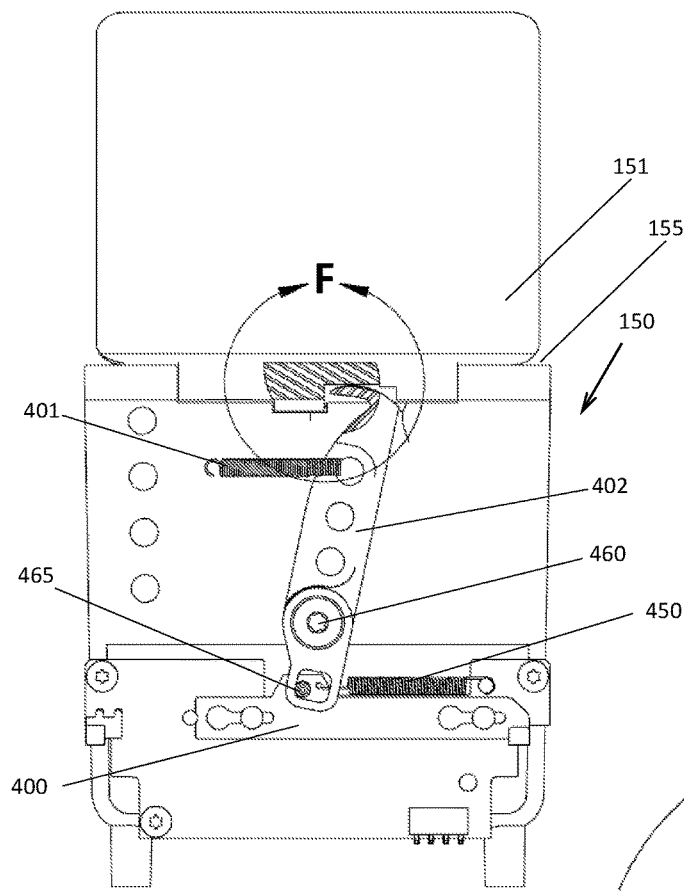
FIG. 19 is a rear partial section view of the bin embodiment shown in FIG. 17 where the bin has been opened and where the location for Detail F has been shown.

FIG. 19 is a rear partial section view of the bin embodiment shown in FIG. 17 where the bin 150 has been opened and where the location for Detail F has been shown. When the bin 150 is opened, each of the springs 401 and 450 may be stretched due to the movement of the actuator 400.

Figure 20:
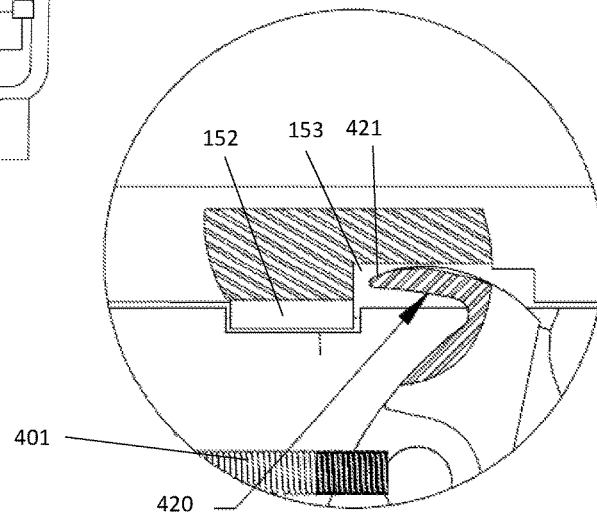
FIG. 20 is a detailed view of Detail F.

FIG. 20 is a detailed view of Detail F. When the bin 150 is unlocked, the lock 402 may rotate so that the hook 420 moves away from the slot 152 and into the open space 153. In this way, the hook 420 is disengaged from the lid 151 so that it can open. When open, a top portion of the hook 420 may be in contact with or close to contact with the top portion of the open space 153. As the lid 151 is closed, the top portion of the open space 153 should contact the top portion of the hook 420, in order to guide the hook 420 into the slot 152 in order to re-lock the bin 150. In an exemplary embodiment, the rounded tip 421 of the hook 420 may contact a portion of the open space 153 or the opening of the slot 152 in order to further guide the tip 421 into the slot 152 and thus ensure that the hook 420 becomes engaged within the slot 152.

Figure 21:
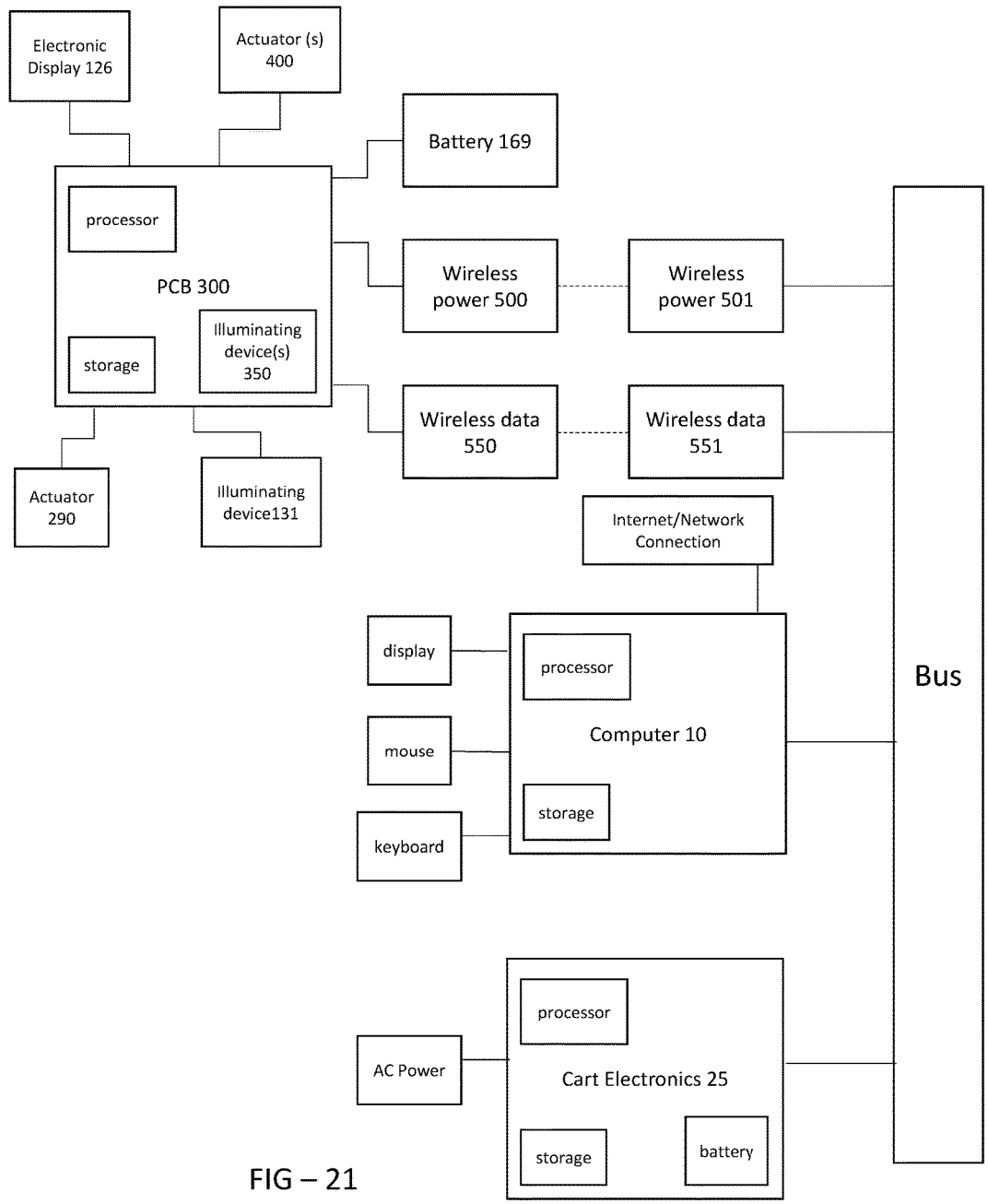
FIG. 21 is an electrical block diagram of an exemplary embodiment of the medical cart.

FIG. 21 is an electrical block diagram of an exemplary embodiment of the medical cart.

The delivery module 110 includes a PCB 300 which preferably has both a processor and electronic storage. A number of different types of data can be stored on this electronic storage, including but not limited to: destination for the module 110, date/time for the last time the module 110 was opened and which bin 150 was accessed, battery 169 levels, and identifying information data for the module 110 (serial number, model number, customer number, etc.). Any of this data can be stored on the display module 110 and displayed on the display 126, before/after/during delivery or transportation and because of the geometry of the protrusion and drawer, can even display to a user when the module 110 is closed within a drawer. Any of this data can also be transmitted to the processor either on the computer 10 or the cart electronics 25 either once the module 110 has been installed within the drawer and electrical communication between the wireless data transmitter/receivers 550 and 551 is established. Any of this data can also be transmitted to the processor either on the computer 10 or the cart electronics 25 either once the module 110 has been installed within the drawer and electrical communication between the wireless data transmitter/receivers 550 and 551 is established or through the internet/network connection with the computer 10, which can be a wired or wireless connection. Thus, the cart can receive the data for the module 110 through the internet/network connection prior to the module 110 actually being installed within the cart. In this way, the cart knows the modules 110 that are intended for install and when the cart recognized that a module 110 is not intended for the cart and (1) an error message can be displayed and/or (2) the lock 270 can be electronically unlocked when the data for the module 110 does not match the data for a module 110 that is intended for the cart.

Figure 22:
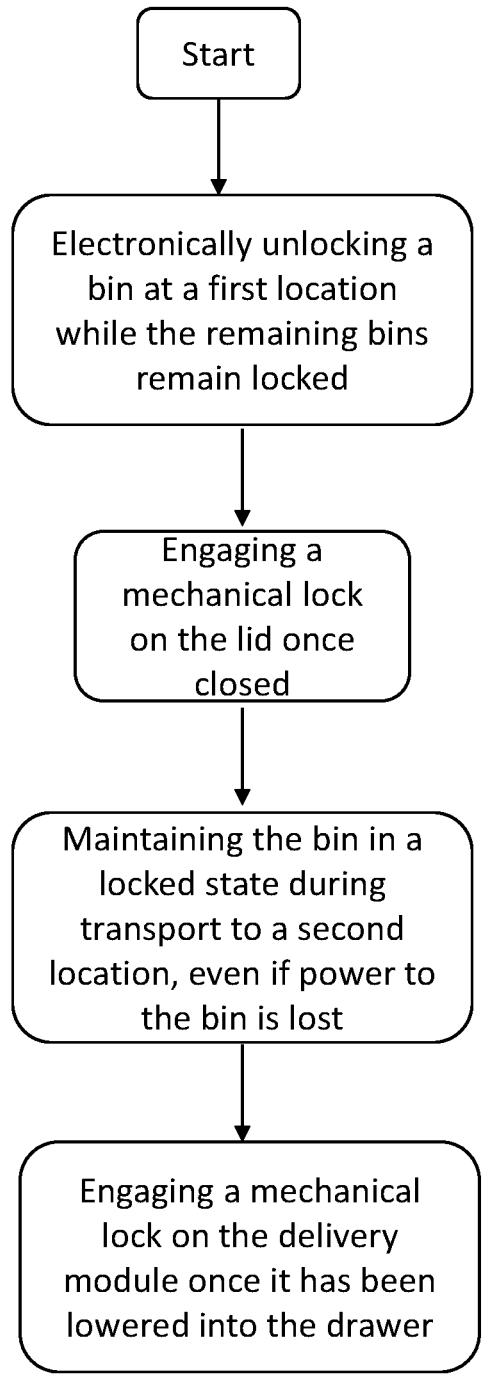
FIGS. 22-25 are logical flowcharts for performing a method of controlling access to medications.
Figure 23:
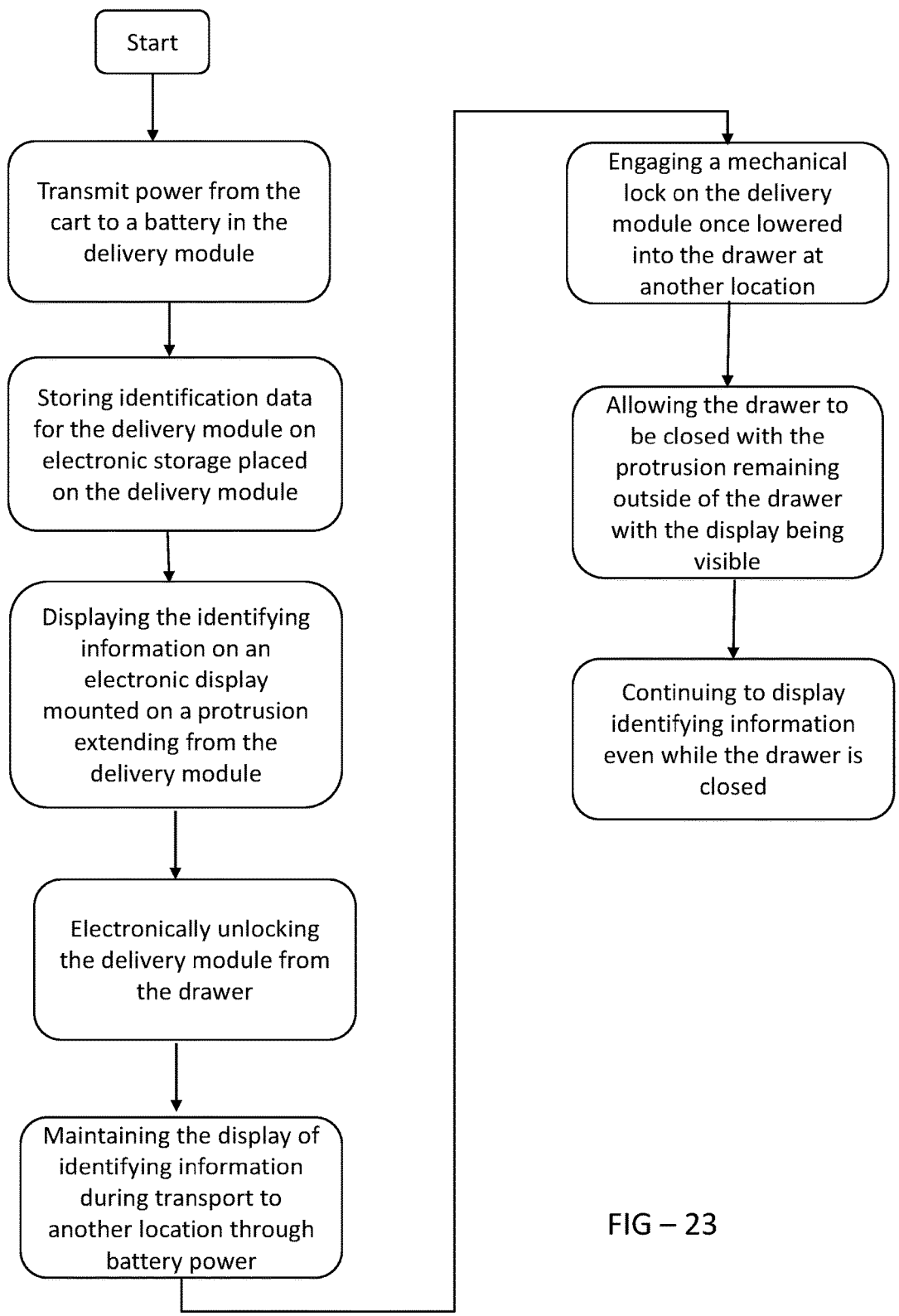

FIGS. 22-25 are logical flowcharts for performing a method of controlling access to medications. In FIG. 22, the mechanical lock 402 on the bins 150 should preferably engage automatically by the system once the lid 151 has been lowered adequately. As described above, the spring(s) are preferably biased to maintain a locked orientation, such that even if the battery 169 were to lose power, the bin 150 would remain locked.

Figure 24:
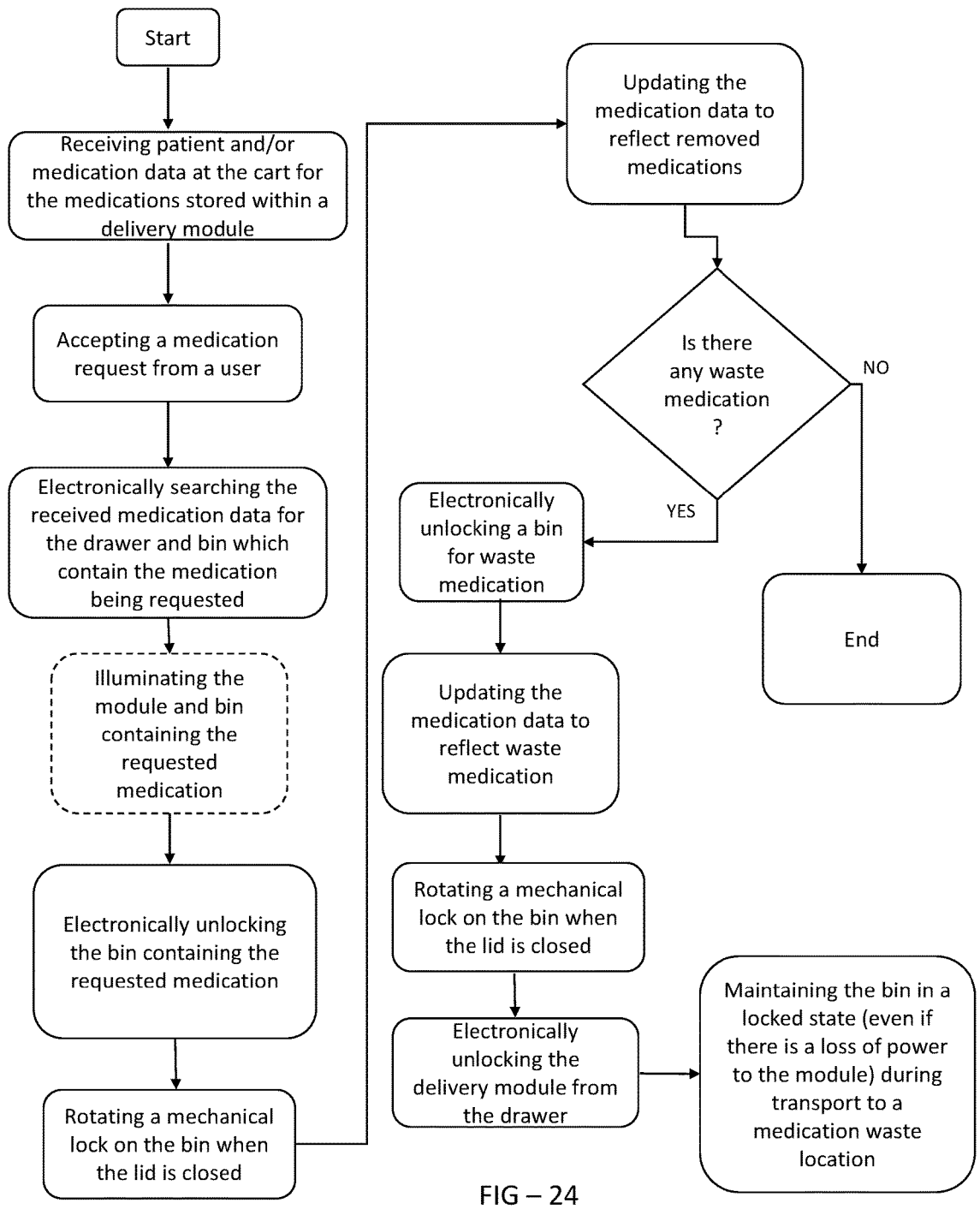
Figure 25:
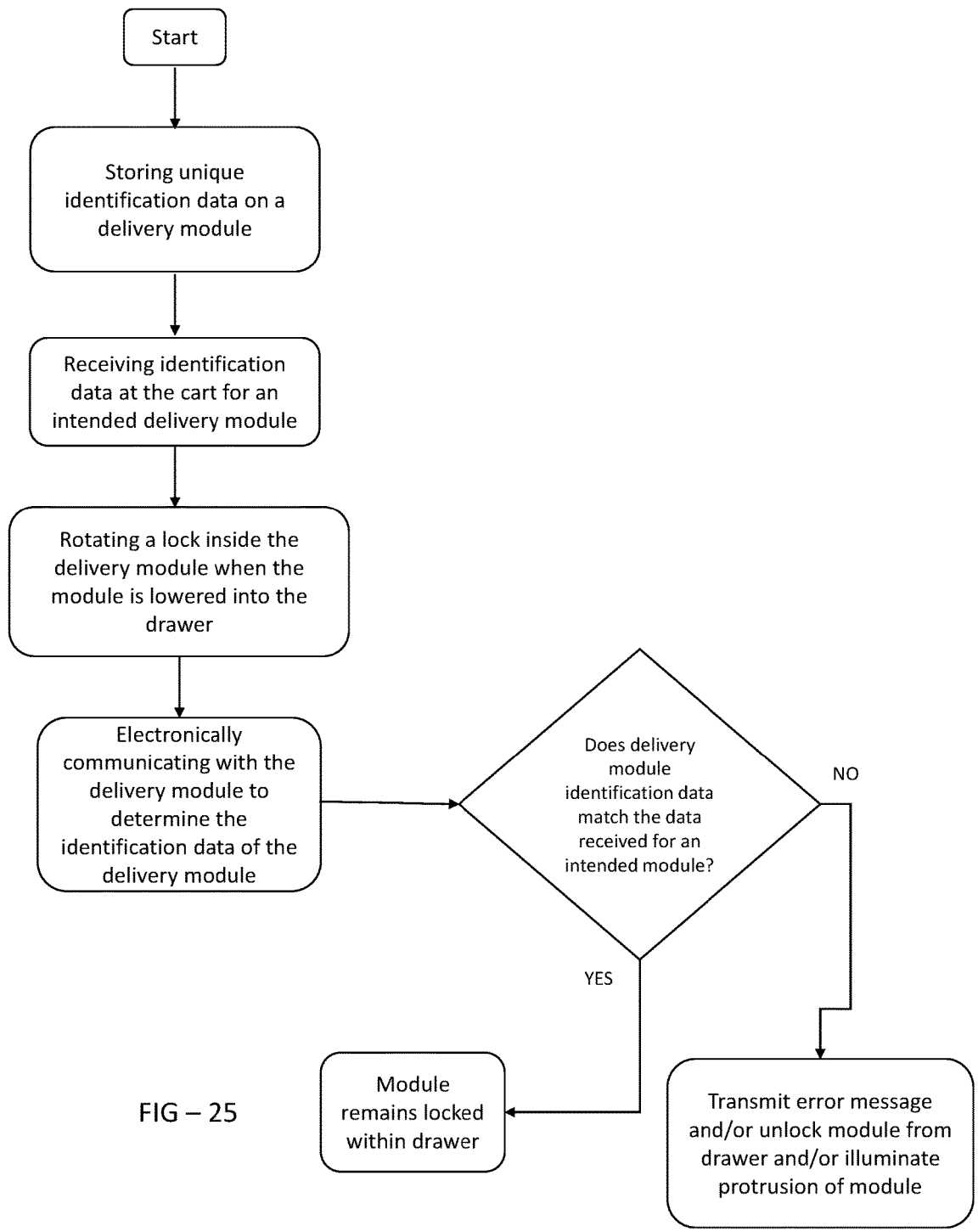

Regarding FIG. 24, as noted above there is a number of different types of data regarding the module and its contents which can be transmitted to the cart, either through the module 110 itself or through the network/internet connection on the cart. When medications are placed within a bin 150, the medication data (optionally including the patient for whom the medication is intended) can be stored, preferably including the module 110 and bin 150 containing the medication. This can be stored on a server or computer and accessed by the system through the network/internet connection on the computer 10. When a user accesses the cart, specific medications stored in a module 110 may be searched for, or specific patients may be searched for, in order to find their corresponding medications. All of this data can be input, searched, and/or accessed through the electronic storage and processors outlined above with a user interface that can be accessed from computer 10 and various input means described above. Once the bin 150 and/or module 110 containing the requested medication has been located, the bin 150 or the module 110 can optionally be illuminated as described above. When there is waste medication, either already removed and was not administered or medication that was never removed, the data stored can be updated to indicate the waste medication and the module 110 and bin 150 that now contain the waste medication. Any module 110 containing waste (i.e. waste module) can then have each bin 150 locked before being transported to a medication waste location, which can either be returned to the original pharmacy or distribution center or can be taken to a waste-specific location that is not necessarily the origin of the medications.

It is respectfully noted that although power to the delivery module is preferably shown as wireless power 500/501, this is not required, as any person of ordinary skill could also use connectors which would establish an electrical connection when the delivery module is installed within the drawer. Similarly, although electronic data transmission to and from the delivery module is shown as wireless data 550/551, this is not required, as connectors could be used for this as well.

It should be noted that the bins 150 can be used to store and transport any item that requires some type of security. Generally, this would include medications and medical supplies (such as instruments, devices, etc.) but could also apply to any item having value, either from being rare or from a high price point for purchase. Thus, although described as a "medical cart" herein, the structure and teachings can be used for any other small items that require tracking and secure transport.

Having shown and described a preferred embodiment of the invention, those skilled in the art will realize that many variations and modifications may be made to affect the described invention and still be within the scope of the claimed invention. Additionally, many of the elements indicated above may be altered or replaced by different elements which will provide the same result and fall within the spirit of the claimed invention. It is the intention, therefore, to limit the invention only as indicated by the scope of the claims.

We claim:
1. A medical cart comprising:
   a drawer having a post which extends upwardly from a bottom surface of the drawer; and
   a removable medication delivery module having
      four sidewalls and a bottom wall;
      a plurality of individually-lockable bins placed above the bottom wall and within the four sidewalls;
      a lock positioned above the bottom wall and below the plurality of individually-lockable bins;
      an aperture on the lock which engages with the post; and
      a hole in the bottom wall sized to accept the post.
2. The medical cart of claim 1 further comprising:
   a printed circuit board (PCB) placed between the lock and the plurality of bins.
3. The medical cart of claim 2 further comprising:
   a battery placed between a bin and one of the four sidewalls and in electrical communication with the PCB.
4. The medical cart of claim 1 wherein:
   the four sidewalls of the removable medication delivery module are sized to fit within the drawer.
5. The medical cart of claim 1 wherein:
   the post comprises
      a first shaft of diameter D1 extending from the bottom surface of the drawer;
      a second shaft of diameter D2 extending upwardly from the first shaft; and
      a tip which extends upwardly from the second shaft.
6. The medical cart of claim 5 wherein:
   diameter D1>diameter D2.
7. The medical cart of claim 5 wherein:
   the tip has a conical shape.
8. The medical cart of claim 5 wherein:
   the lock engages with the second shaft of the post and is located below the tip when engaged.
9. A medical cart comprising:
   a drawer having a front wall and a post which extends upwardly from a bottom surface of the drawer, and
   a removable medication delivery module having
      a front sidewall and a bottom wall,
      a plurality of bins placed above the bottom wall,
      a lock positioned above the bottom wall and below the plurality of bins,
      an aperture on the lock which engages with the post, and
      a protrusion which extends forwardly from the front sidewall and contains an opening which faces downward; and
   a notch placed on the front wall of the drawer and sized to allow the protrusion of the removable medication delivery module to extend through and away from the front wall of the drawer.
10. The medical cart of claim 9 further comprising:
    a spring positioned between the bottom surface of the drawer and the bottom wall of the removable medication delivery module.
11. The medical cart of claim 9 further comprising:
    an illuminating device positioned to direct light into the opening of the protrusion.
12. The medical cart of claim 9 wherein:
    the protrusion begins by extending horizontally and forwardly from the front sidewall of the removable medication delivery module before curving downwardly and ending nearly perpendicular to the front sidewall.

13. The medical cart of claim 9 further comprising:
an electronic display positioned on the protrusion.

14. The medical cart of claim 9 wherein:
each bin contains a lid which is hingedly fastened to the bin such that the hinge is located on a side of the bin that is opposite a side of the bin facing the front sidewall of the removable medication delivery module.

15. The medical cart of claim 13 wherein:
the protrusion contains a substantially horizontal portion extending from the front sidewall of the removable medication delivery module, a curved portion connecting with the substantially horizontal portion, and a substantially vertical portion connecting to the curved portion; and
the electronic display is positioned on the curved portion.

16. A medical cart comprising:
a drawer having a bottom surface;
a pair of posts which extend upwardly from the bottom surface of the drawer and each comprise
 a first shaft of diameter D1 extending from the bottom surface of the drawer,
 a second shaft of diameter D2 extending upwardly from the first shaft, and
 a tip which extends upwardly from the second shaft; and
a removable medication delivery module having
 four sidewalls and a bottom wall;
 a plurality of bins placed above the bottom wall and within the four sidewalls;
 an elongate lock having a pair of opposing ends and positioned above the bottom wall and below the plurality of bins;
 an aperture on each opposing end of the lock which engages with the second shaft of the post;
 a pivot point placed near a center point of the elongate lock, pivotally attaching the elongate lock to the bottom wall of the removable medication delivery module and
 a pair of holes in the bottom wall sized to accept the pair of posts.

17. The medical cart of claim 16 further comprising:
a printed circuit board (PCB) placed between each bin and the elongate lock; and
an illuminating device positioned on the PCB and underneath each bin to direct light upwardly into the bin.

18. The medical cart of claim 16 further comprising:
an extension spring having two ends where the first end is attached to the bottom wall and the second end is attached to the elongate lock.

19. The medical cart of claim 18 further comprising:
an electromechanical actuator attached to the bottom wall; and
a linkage oriented substantially parallel to the extension spring and having a pair of opposing ends where the first end is attached to the electromechanical actuator and the second end is attached to the elongate lock.

* * * * *